United States Patent
Jeon

(10) Patent No.: US 10,507,287 B2
(45) Date of Patent: Dec. 17, 2019

(54) NEEDLELESS DRUG DELIVERY SYSTEM

(71) Applicant: JSKBIOMED INC., Daejeon (KR)

(72) Inventor: Jin Woo Jeon, Incheon (KR)

( * ) Notice: Subject to any disclaimer, the term of this patent is extended or adjusted under 35 U.S.C. 154(b) by 265 days.

(21) Appl. No.: 15/631,242

(22) Filed: Jun. 23, 2017

(65) Prior Publication Data

US 2018/0126079 A1    May 10, 2018

(30) Foreign Application Priority Data

Nov. 10, 2016 (KR) .......................... 10-2016-0149310

(51) Int. Cl.
*A61M 5/30* (2006.01)

(52) U.S. Cl.
CPC .................... *A61M 5/30* (2013.01)

(58) Field of Classification Search
CPC .... A61M 5/2046; A61M 5/30; A61M 1/1037; A61M 5/282; A61M 5/204; A61M 2205/36; A61M 5/31511; A61M 5/20; A61M 5/28; A61M 5/281; A61M 5/3007
USPC .......................................................... 604/70
See application file for complete search history.

(56) References Cited

U.S. PATENT DOCUMENTS

| | | | | |
|---|---|---|---|---|
| 1,637,219 | A | * | 7/1927 | Edelmann .............. G01L 19/00 222/206 |
| 5,848,993 | A | * | 12/1998 | Tanhehco ............. A61M 1/0011 604/217 |
| 8,905,966 | B2 | * | 12/2014 | Yoh ........................ A61M 5/30 604/140 |
| 2003/0114789 | A1 | | 6/2003 | Haar et al. |
| 2003/0149396 | A1 | | 8/2003 | Alexandre et al. |
| 2011/0230826 | A1 | * | 9/2011 | Yoh ........................ A61M 5/30 604/70 |
| 2013/0042753 | A1 | * | 2/2013 | Becker ................ F04B 43/0054 92/96 |

FOREIGN PATENT DOCUMENTS

| | | |
|---|---|---|
| JP | 5731120 | 4/2016 |
| KR | 10-2012-0105718 | 9/2012 |
| KR | 10-1207977 | 11/2012 |
| KR | 10-2014-0021383 | 2/2014 |
| KR | 10-1424394 | 7/2014 |
| KR | 10-2014-0140747 | 12/2014 |
| KR | 10-1500568 | 3/2015 |
| KR | 10-1549966 | 8/2015 |
| KR | 10-1684250 | 12/2016 |
| WO | 0023132 | 4/2000 |
| WO | 2008114223 A1 | 9/2008 |
| WO | 2017140974 | 8/2017 |

OTHER PUBLICATIONS

Exonic Polymers, Nitrile (NBR) Rubber Material Specs, Accessed Feb. 26, 2019, https://www.exonicpolymers.com/Articles.asp?ID= 265 (Year: 2019).*

\* cited by examiner

*Primary Examiner* — Jason E Flick
(74) *Attorney, Agent, or Firm* — Jake K. Lee; Lee & Associates LLC

(57) ABSTRACT

The present invention relates generally to a needleless drug delivery system. More particularly, the present invention relates to a needleless drug delivery system, in which durability of a membrane that partitions a space to fill a drug is enhanced by reinforcing a weak portion of the membrane or by forming a double membrane.

8 Claims, 8 Drawing Sheets

NEEDLELESS DRUG DELIVERY SYSTEM

CROSS REFERENCE TO RELATED APPLICATION

The present application claims priority to Korean Patent Application No. 10-2016-0149310, filed Nov. 10, 2016, the entire contents of which is incorporated by reference herein for all purposes.

BACKGROUND

Field of the Invention

The present invention relates generally to a needleless drug delivery system. More particularly, the present invention relates to a needleless drug delivery system, in which durability of a membrane that partitions a space to fill a drug is enhanced by reinforcing a weak portion of the membrane or by forming a double membrane.

Description of the Related Art

Generally, drug delivery system is a system designed to deliver the required amount of drug efficiently into the body by minimizing the side effects that occur in conventional methods and by maximizing the therapeutic effects of the drug when using a drug for the treatment of diseases or wounds of the human body.

Of various types of drug delivery methods that are currently used, the needle injection method is the most common because of its stability and efficiency.

The drug delivery system using a needle is capable of accurate and efficient drug administration, but it has problems such as needle phobia due to injection pain, risk of infection due to reuse, and producing a large amount of medical waste.

To solve the above problems, several new methods, such as powder injection, liquid jet injection, a microneedle, and the like, have been studied to develop a new drug delivery system, but there are still problems to be solved.

A method using a liquid jet with a piezo actuator injects a drug liquid at a high speed to penetrate the skin tissue and infiltrate the drug. This method was first attempted in the 1930s, it has been used to deliver many kinds of macromolecules, drugs such as insulin and growth hormone, and vaccines to the body, but it has not become popularized due to problems such as splash back during jet injection, instability of delivered drug volume and penetration depth, and considerable pain to the recipient.

Instead of the above method using the piezo actuator, a micro jet injector using a laser-induced shockwave has recently been developed. Among the drug delivery systems that have been studied recently, a biolistic method which directly accelerates microparticles and a drug jet delivery method which injects a drug solution in the form of a jet, are expected to solve the problems of needle phobia, pain, and wounds, which are the biggest weaknesses of existing delivery systems.

The laser can concentrate extremely high energy on a very small localized area, and its controllability and stability are also excellent. Further, laser equipment can be miniaturized by using an optical fiber, and thereby it is also possible to deliver drugs to human body.

The micro jet injector using a laser-induced shockwave includes: a pulse laser beam used as a power source for liquid jet that discharges a drug finely; a chamber accommodating a solution and the drug; a separation membrane separating the solution and the drug; and a nozzle having a diameter of 100 μm or less for discharging the liquid jet, wherein when the pulse laser beam is focused on a pressure chamber filled with a liquid, explosive phase changes occur due to the instantaneous high energy transfer to a local area and the substances around it are evaporated instantaneously, causing bubbles, whereby the pressure in the pressure chamber rises (volume expansion due to shockwaves and bubbles) and the separation membrane expands toward the drug, and the expansion of the separation membrane pushes the drug out of the nozzle, generating a high pressure at an outlet of the nozzle, whereby the drug that passes through the nozzle with the diameter of 100 μm or less is sprayed as liquid jets each having a diameter of 100 μm or less at high speed.

However, it is problematic in that the edge and the center of the separation membrane may be damaged due to the rapid expansion of the separation membrane.

The document of Korean Patent No. 10-1207977 discloses a micro jet drug delivery system.

The foregoing is intended merely to aid in the understanding of the background of the present invention, and is not intended to mean that the present invention falls within the purview of the related art that is already known to those skilled in the art.

SUMMARY

Accordingly, the present invention has been made keeping in mind the above problems occurring in the related art, and the present invention is intended to propose a needleless drug delivery system, in which the durability of a membrane that partitions a space to fill a drug is enhanced by reinforcing a weak portion of the membrane or by forming a double membrane.

Objects of embodiments of the present invention are not limited to the forgoing object, and other and further objects, features, and advantages of the invention will appear more fully from the following description.

In order to achieve the above object, according to an embodiment of the present invention, there is provided a needleless drug delivery system including: an upper housing 100 including: a pressure side wall 110 provided to form a side surface of the upper housing with an end wall closing one end of the pressure side wall; and a transmissive lens 120 provided at the end wall; a lower housing 200 including: a drug side wall 210 provided to form a side surface of the lower housing; and a discharge nozzle 230 provided by extending from the drug side wall 210 and provided with a discharge hole 231, wherein the lower housing is connected with or extends from the upper housing 100; and a separation membrane 300 of elastic material provided between the upper housing 100 and the lower housing 200 to separate the upper housing 100 and the lower housing 200, wherein a space of the upper housing 100 having the transmissive lens 120 is hermetically filled with a pressure-generating fluid 101, and the separation membrane 300 includes: an edge reinforcing portion 310 protruding along an edge of the separation membrane 300; a center reinforcing portion 320 protruding from a center of the separation membrane 300; and a plurality of connection reinforcing portions 330 each protruding in a shape that connects any one point of the edge reinforcing portion 310 and the center reinforcing portion 320.

Further, the center reinforcing portion 320 may be made of a reflective or an opaque material at a surface thereof facing the transmissive lens 120.

Further, the connection reinforcing portions 330 may be formed radially about the center reinforcing portion 320.

Further, the connection reinforcing portions 330 may be configured such that angles between the connection reinforcing portions 330 are same.

In order to achieve the above object, according to an embodiment of the present invention, there is provided a needleless drug delivery system including: an upper housing 100 including: a pressure side wall 110 provided to form a side surface of the upper housing with an end wall closing one end of the pressure side wall; and a transmissive lens 120 provided at the end wall; a lower housing 200 including: a drug side wall 210 provided to form a side surface of the lower housing; and a discharge nozzle 230 provided by extending from the drug side wall 210 and provided with a discharge hole 231, wherein the lower housing is connected with or extends from the upper housing 100; a separation membrane 300 of elastic material provided between the upper housing 100 and the lower housing 200 to separate the upper housing 100 and the lower housing 200; and a partition membrane 400 of elastic material provided in the upper housing 100 being spaced apart from the separation membrane 300 at a predetermined interval to partition the upper housing 100, wherein a space between the partition membrane 400 and the transmissive lens 120 is hermetically filled with a pressure-generating fluid 101, and a space between the partition membrane 400 and the separation membrane 300 is hermetically filled with a pressure-transmitting fluid 102.

Further, the separation membrane 300 may be made of a reflective or an opaque material.

Further, the partition membrane 400 may be made of a reflective or an opaque material.

Further, the pressure-generating fluid 101 may be a liquid or an opaque liquid mixed with a reflector or an opaque material.

The needleless drug delivery system may further include an energy-focusing device 500 configured to focus energy toward a predetermined point of the space hermetically filled with the pressure-generating fluid 101.

The lower housing 200 may further include a drug replenishment hole 220 formed with a channel formed through the drug side wall 210 to supply a drug, and the needleless drug delivery system may further include a drug supply unit 600 connected to the drug replenishment hole 220 to supply the drug.

According to an embodiment of the present invention, the needleless drug delivery system is advantageous in that since a weak portion of the separation membrane that separates the space to fill the drug is reinforced by the edge reinforcing portion, the center reinforcing portion, and the connection reinforcing portion, it is possible to enhance durability of the membrane.

The needleless drug delivery system is further advantageous in that since a membrane that separates a space to fill a drug is in the form of a double membrane structure constituted by both the separation membrane and the partition membrane, it is possible to enhance durability of the membrane.

The needleless drug delivery system is further advantageous in that since the center reinforcing portion, the separation membrane, the partition membrane, the pressure-generating fluid, and the like are configured to have reflective or opaque properties, it is possible to prevent deterioration of a drug solution caused by a laser reaching the drug when the laser is focused on a space filled with a pressure-generating fluid.

The needleless drug delivery system is further advantageous in that since the connection reinforcing portions are formed radially to minimize the volume occupied by the connection reinforcing portions, it is possible to reduce manufacturing cost of the reinforced separation membrane.

The needleless drug delivery system is further advantageous in that since angles between a connection reinforcing portion and a neighboring connection reinforcing portion are the same, it is possible to prolong the life of the separation membrane by evenly dispersing stress (pressure, etc.) applied to the separation membrane.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
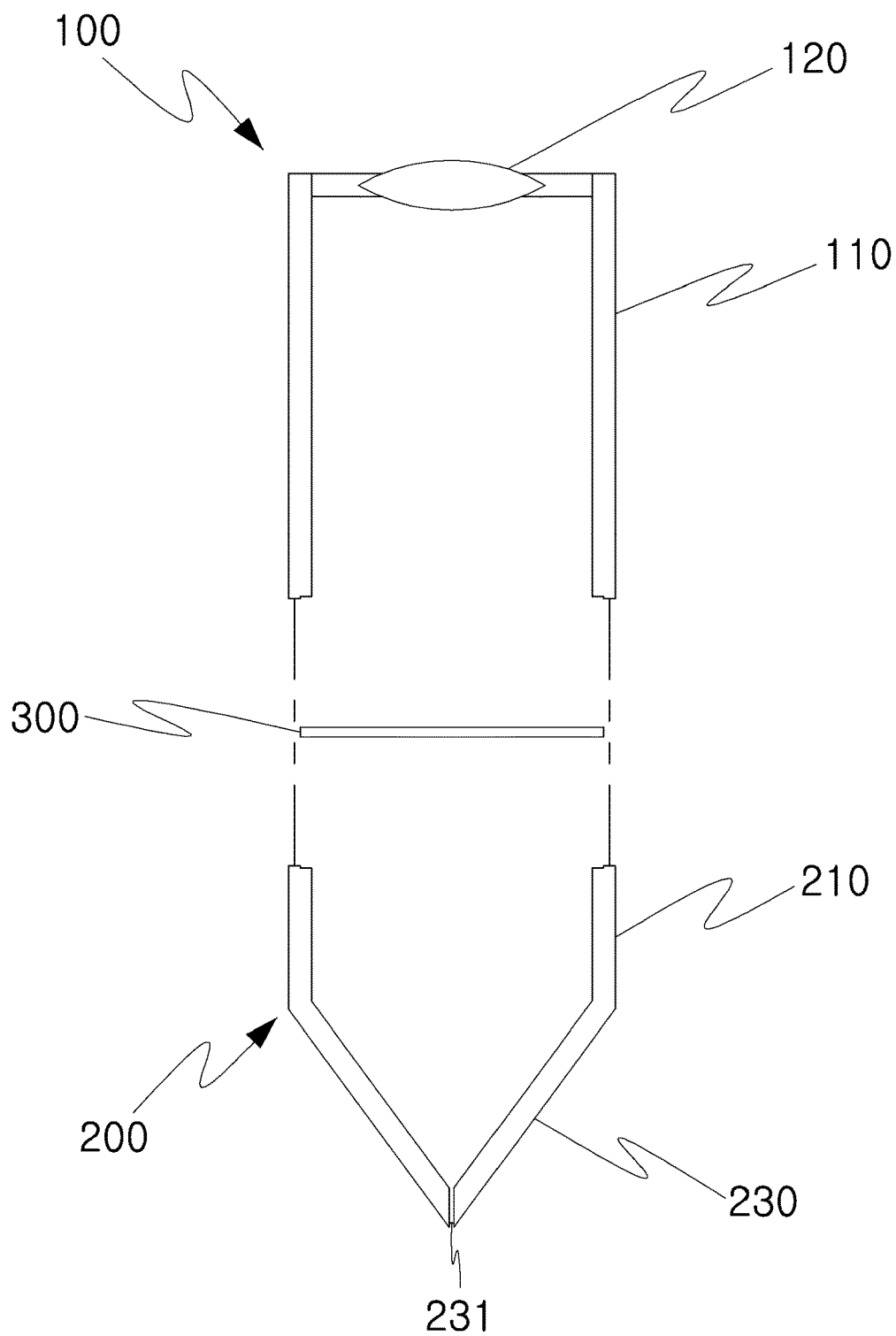
FIG. 1 shows an exploded view of a needleless drug delivery system according to an embodiment of the present invention.

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

It will be understood that when an element is referred to as being "coupled" or "connected" to another element, it can be directly coupled or connected to the other element or intervening elements may be present therebetween.

In contrast, it should be understood that when an element is referred to as being "directly coupled" or "directly connected" to another element, there are no intervening elements present.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

With reference to the accompanying drawings, the present invention will be described in detail herein below. However, in the following description of the invention, if the related known functions or specific instructions on configuring the gist of the present invention unnecessarily obscure the gist of the invention, the detailed description thereof will be omitted. Accordingly, the present invention is not limited to the drawings presented below and may be embodied in other forms. Further, throughout the drawings, the same reference numerals will refer to the same or like parts.

Figure 2:
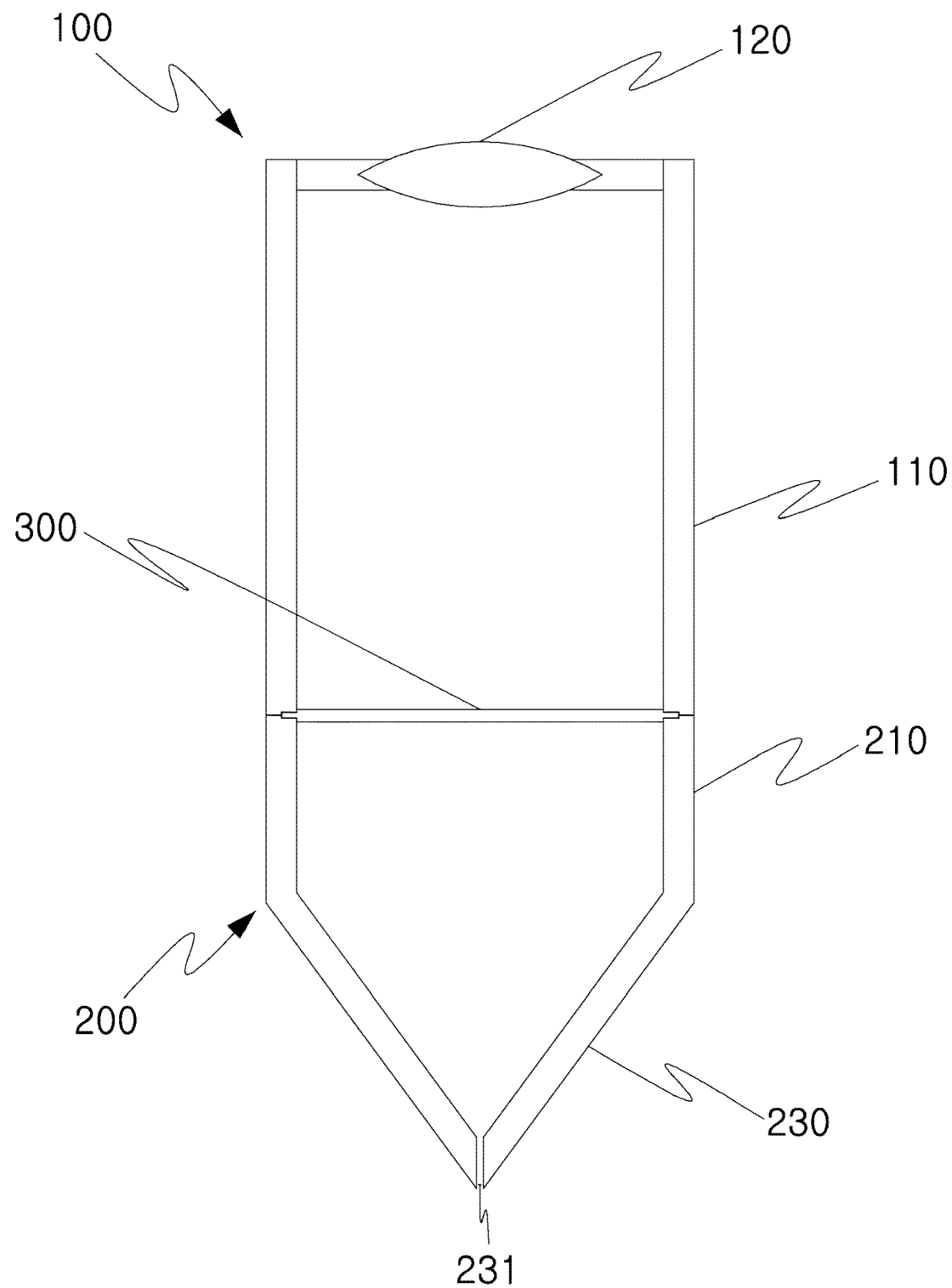
FIG. 2 shows a conceptual view of an assembled state of the needleless drug delivery system according to the embodiment of the present invention.
Figure 3:
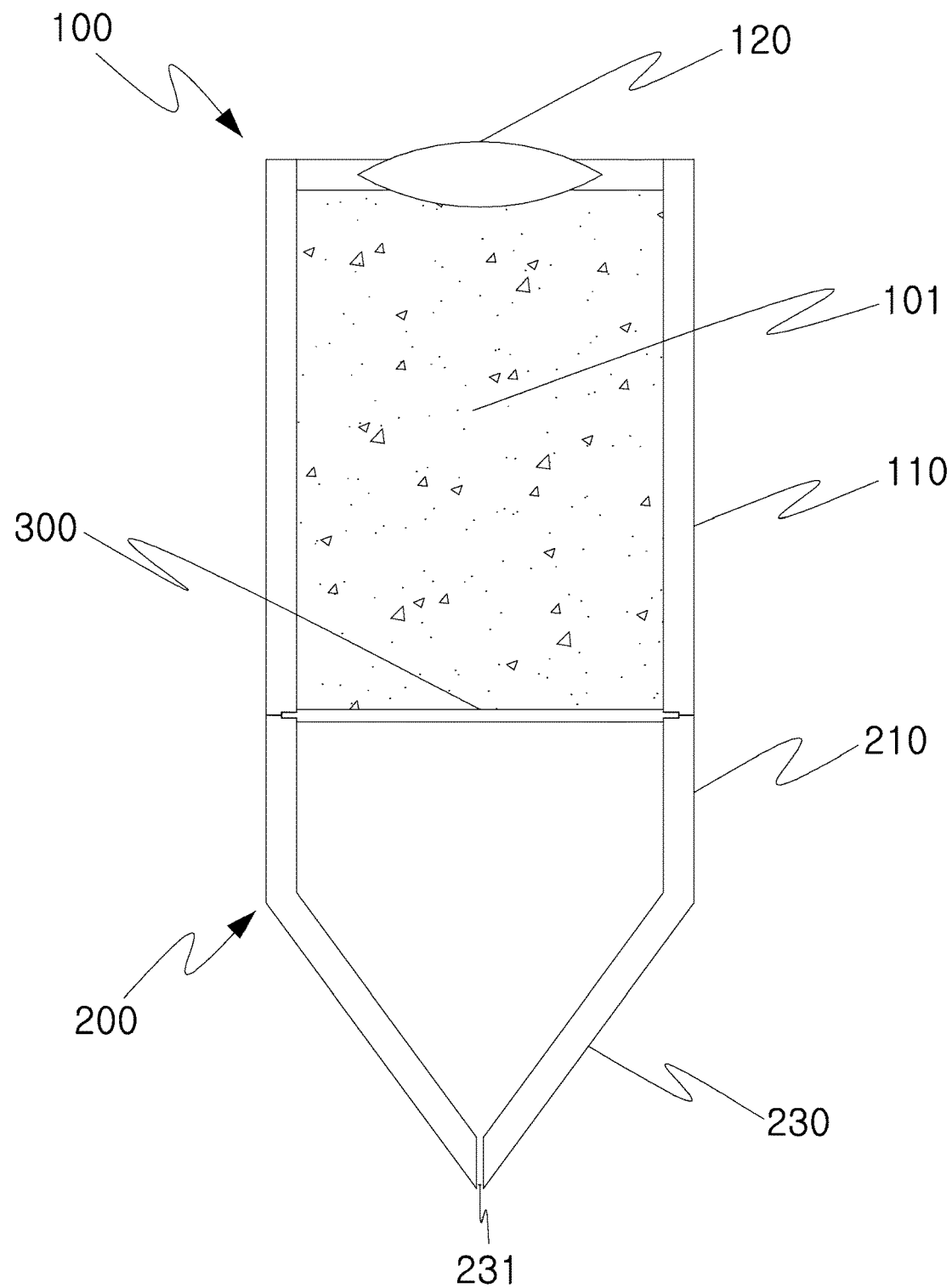
FIG. 3 shows a conceptual view of a state where a pressure-generating fluid is filled in the needleless drug delivery system of FIG. 2.
Figure 4:
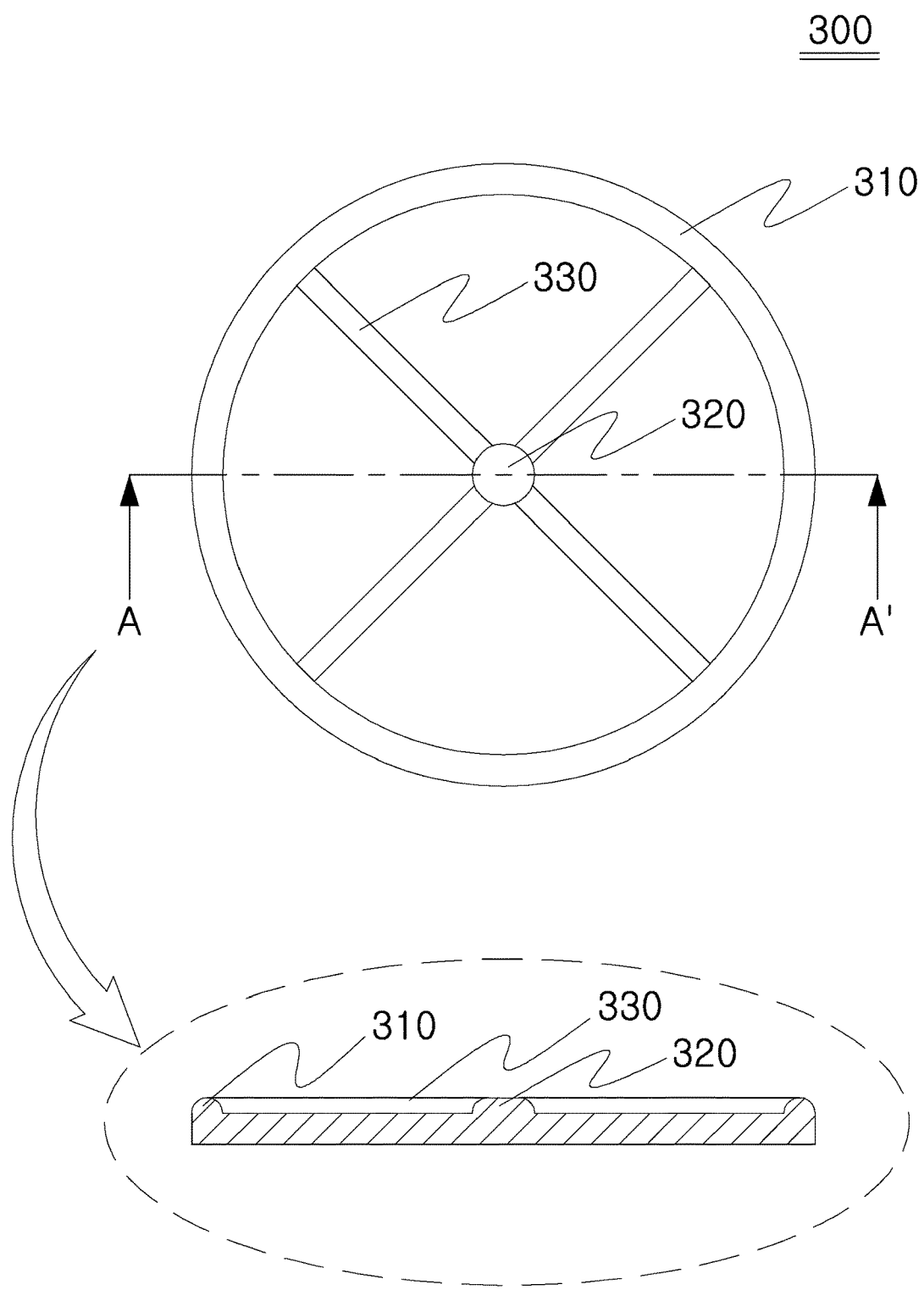
FIG. 4 shows a plane view of a separation membrane of FIG. 1 and a sectional view taken along line A-A.
Figure 5:
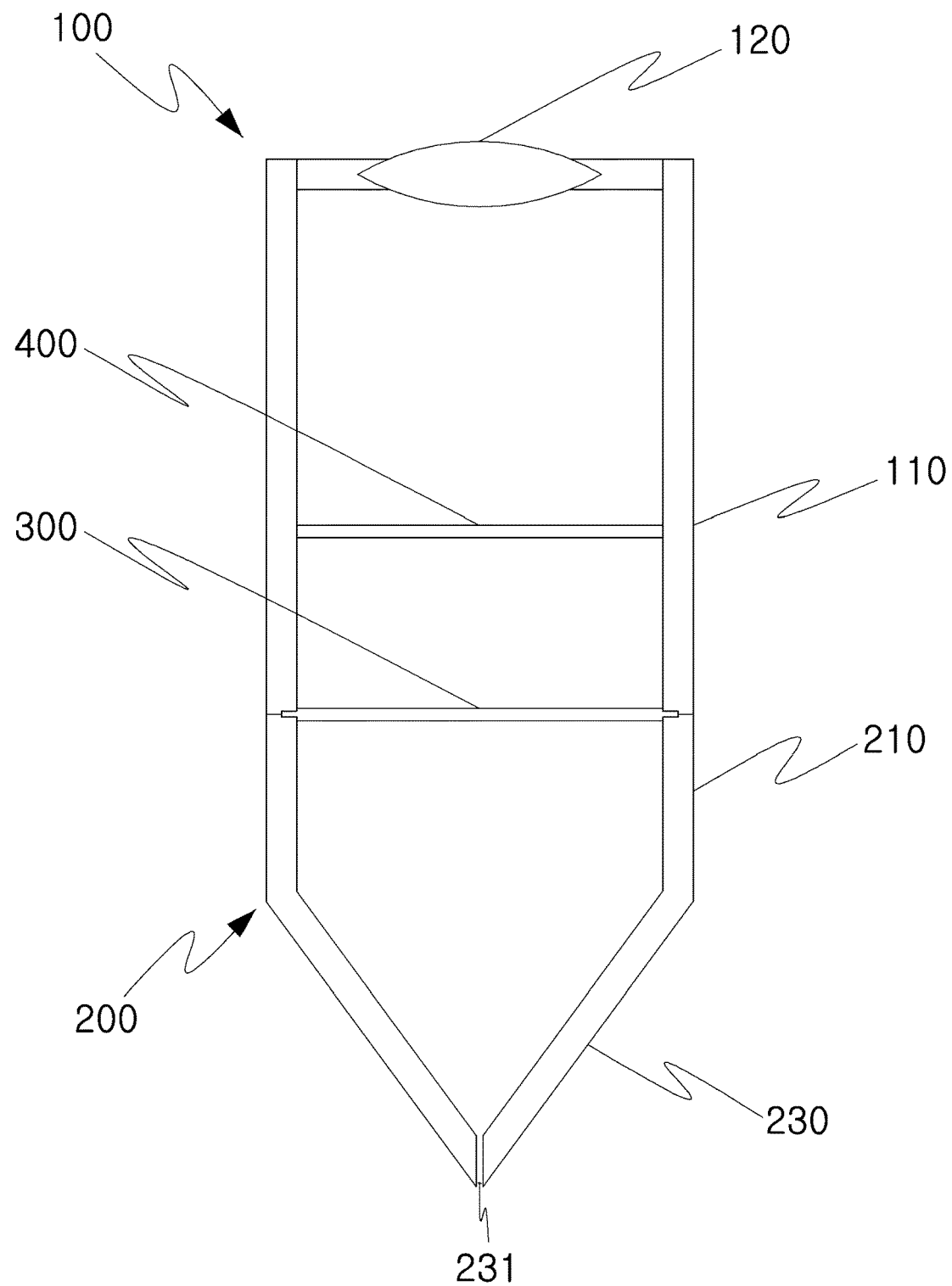
FIG. 5 shows a conceptual view of a needleless drug delivery system according to another embodiment of the present invention.
Figure 6:
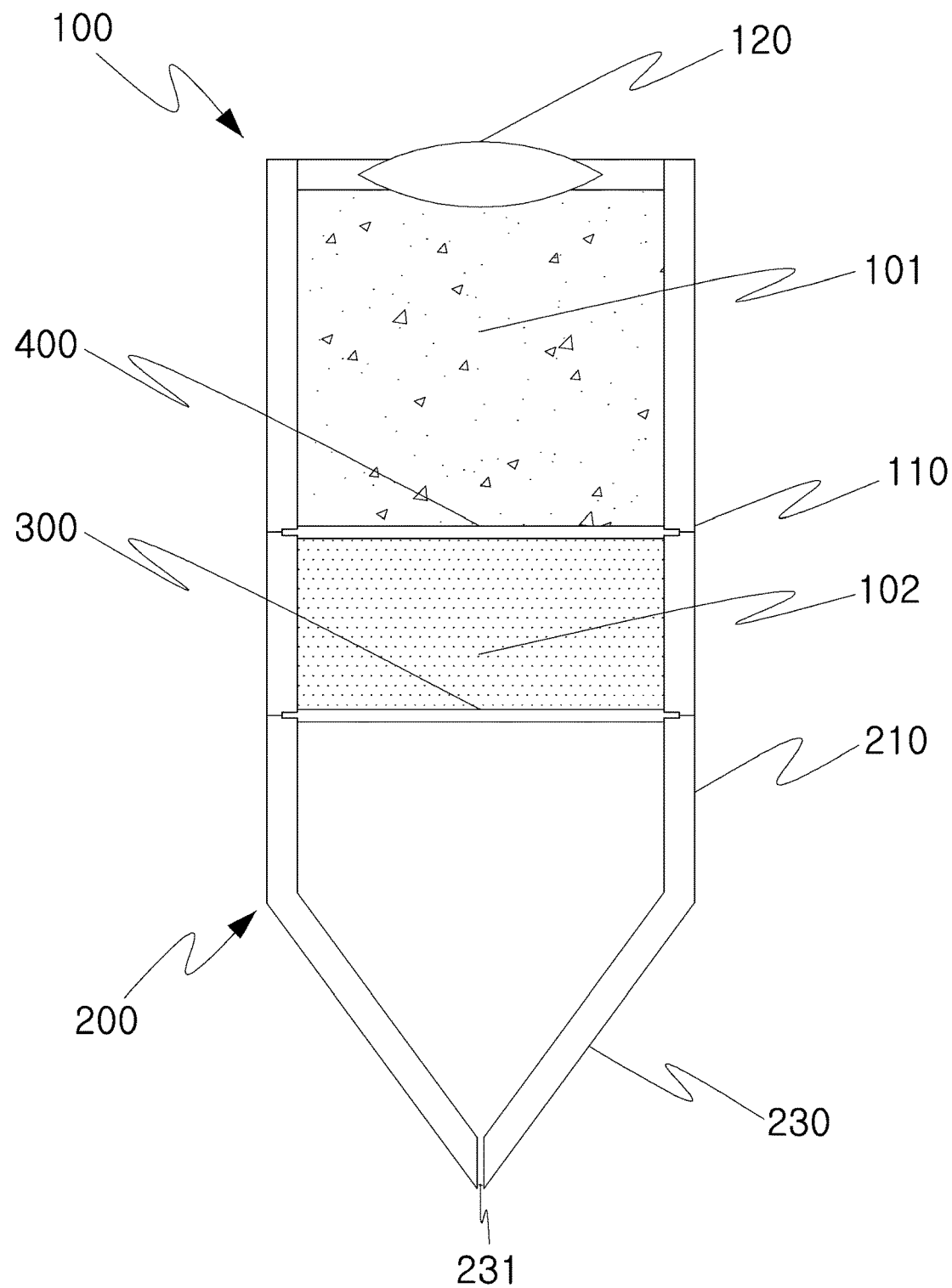
FIG. 6 shows a conceptual view of a state where the pressure-generating fluid and a pressure-transmitting fluid are filled in the needleless drug delivery system of FIG. 5.
Figure 7:
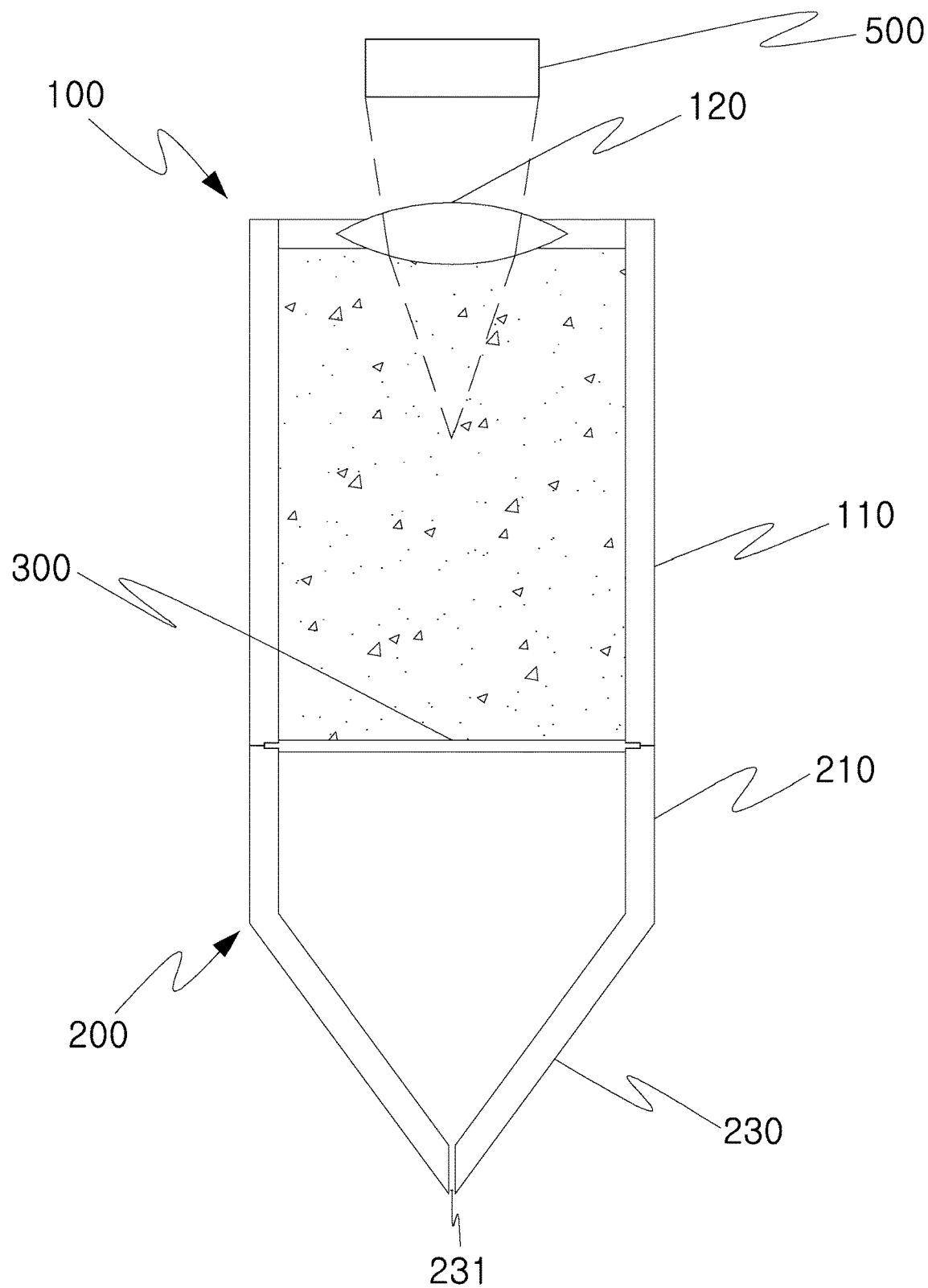
FIG. 7 shows a conceptual view of a state where an energy-focusing device is added to FIG. 3.
Figure 8:
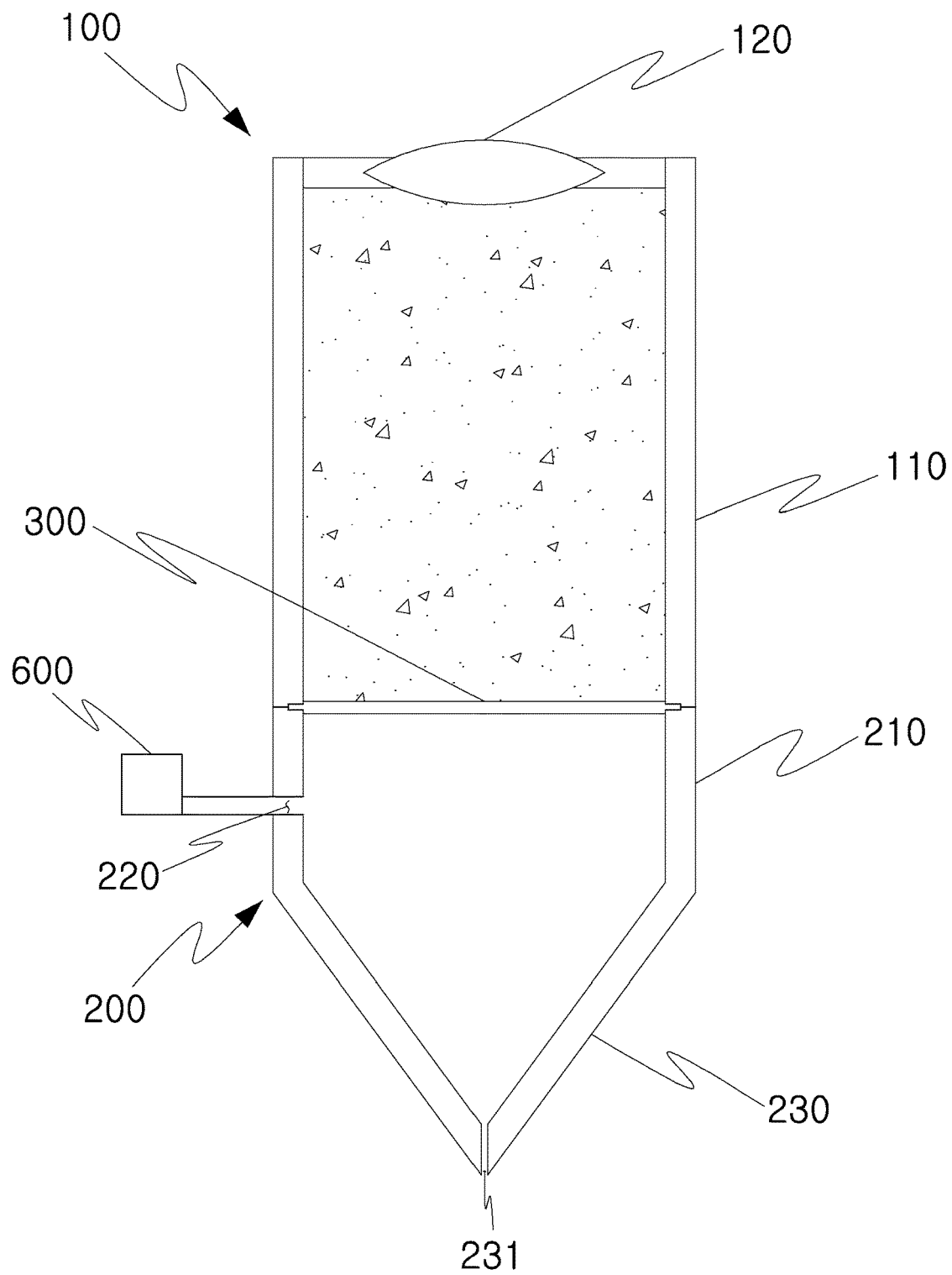
FIG. 8 shows a conceptual view of a state where a drug supply unit is added to FIG. 3.

FIG. 1 shows an exploded view of a needleless drug delivery system according to an embodiment of the present invention; FIG. 2 shows a conceptual view of an assembled state of the needleless drug delivery system according to the embodiment of the present invention; FIG. 3 shows a conceptual view of a state where a pressure-generating fluid is filled in the needleless drug delivery system of FIG. 2; FIG. 4 shows a plane view of a separation membrane of FIG. 1 and a sectional view taken along line A-A; FIG. 5 shows a conceptual view of a needleless drug delivery system according to another embodiment of the present invention; FIG. 6 shows a conceptual view of a state where the pressure-generating fluid and a pressure-transmitting fluid are filled in the needleless drug delivery system of FIG. 5; FIG. 7 shows a conceptual view of a state where an energy-focusing device is added to FIG. 3; and FIG. 8 shows a conceptual view of a state where a drug supply unit is added to FIG. 3.

As shown in FIGS. 1 to 3, according to an embodiment of the present invention, a needleless drug delivery system includes: a upper housing 100 provided with a transmissive lens 120; a lower housing 200; and a separation membrane 300, wherein a space of the upper housing 100 having the transmissive lens 120 is hermetically filled with a pressure-generating fluid 101.

Here, the pressure-generating fluid 101 may be a liquid or an opaque liquid mixed with a reflector or an opaque material.

This is to prevent deterioration of a drug solution caused by a laser passing through the separation membrane 300 and reaching the drug when the laser is focused on the space filled with the pressure-generating fluid 101.

The upper housing 100 is configured such that a pressure side wall 110 is provided to form a side surface of the upper housing 100 with an end wall closing one end of the pressure side wall 110, and the transmissive lens 120 is provided at the end wall.

The upper housing 100 is provided to form an enclosed space for allowing the pressure-generating fluid 101 to be filled therein, and is configured such that the pressure side wall 110 closes the side surface of the upper housing 100, a first end of the upper housing 100, at which the transmissive lens 120 is provided, is closed, and the separation membrane 300 closes a second end thereof, thereby forming the enclosed space with the pressure-generating fluid 101 filled therein.

In FIGS. 1 to 3, it is exemplified that the transmissive lens 120 is formed in a convex shape, and the transmissive lens 120 closes a portion of the first end of the pressure side wall 110, but the present invention is not limited thereto, and the transmissive lens 120 may be formed in various shape such as a planar or a concave shape, capable of projecting light, and the transmissive lens 120 may close the entire first end of the pressure side wall 100.

The lower housing 200 includes: a drug side wall 210 provided to form a side surface of the lower housing 200; and a discharge nozzle 230 provided by extending from the drug side wall 210 and provided with a discharge hole 231, wherein the lower housing 200 is connected with or extends from the upper housing 100.

The lower housing 200 is provided to form a space for allowing a drug to be filled therein, and is configure such that the drug side wall 210, the discharge nozzle 230, and the separation membrane 300 close the lower housing 200 except the discharge hole 231, thereby forming the space with the drug filled therein.

It is preferred that the discharge hole 231 may be formed to have a diameter of 100 μm or less.

When the discharge hole 231 is formed to have a diameter of 100 μm or less, even if the drug is filled in the space to fill the drug, the drug cannot escape through the discharge hole 231 unless a pressure higher than a predetermined pressure is applied.

Here, the upper housing 100 and the lower housing 200 may be integrally formed with each other, or be detachably formed from each other.

The separation membrane 300 is provided between the upper housing 100 and the lower housing 200, and is made of an elastic material to separate the upper housing 100 and the lower housing 200.

In other words, the separation membrane 300 separates the upper housing 100 and the lower housing 200, to form an enclosed space for allowing the pressure-generating fluid 101 to be filled therein at a side of the separation membrane 300 (over the separation membrane 300 of FIG. 2).

Here, the separation membrane 300 may be made of silicone rubber.

Further, the separation membrane 300 may be made of a reflective or an opaque material.

This is to prevent deterioration of a drug solution caused by a laser passing through the separation membrane 300 and reaching the drug when the laser is focused on the space filled with the pressure-generating fluid.

When the upper housing 100 and the lower housing 200 are detachably formed from each other, it is preferred that the separation membrane 300 is interposed at a junction between the upper housing 100 and the lower housing 200 (see FIGS. 1 to 3).

An edge and a center of the separation membrane 300 may be damaged early due to the rapid expansion of the separation membrane 300. Therefore, it is preferred that the edge and the center of the separation membrane 300 be reinforced.

To this end, as shown in FIG. 4, the separation membrane 300 includes: an edge reinforcing portion 310; a center reinforcing portion 320; and a connection reinforcing portion 330.

In FIG. 4, it is exemplified that the edge reinforcing portion 310, the center reinforcing portion 320, and the connection reinforcing portion 330 protrude upward, but the present invention is not limited thereto, and the reinforcing portions may be formed in any shape that increases a thickness of the separation membrane 300, for example, in a shape protruding downward or in a shape protruding upward and downward.

The edge reinforcing portion 310 protrudes along the edge of the separation membrane 300.

The edge reinforcing portion 310 is provided to reinforce the edge of the separation membrane 300, and is formed by protruding from the edge of the separation membrane 300.

In other words, the edge reinforcing portion 310 is formed more convexly (thicker) than the other portions.

Herein, the edge of the separation membrane 300 is a portion at which the separation membrane 300 is in contact with inner surfaces of the upper housing 100 and the lower housing 200.

When the upper housing 100 and the lower housing 200 are detachably formed from each other, the separation membrane 300 may be interposed at a junction between the upper housing 100 and the lower housing 200, and of the separation membrane 300, a portion pressed by the upper housing 100 and the lower housing 200 may formed to be thickened.

The center reinforcing portion 320 protrudes from a center of the separation membrane 300.

The center reinforcing portion 320 is provided to reinforce the center of the separation membrane 300, and formed by protruding from the center of the separation membrane 300.

In other words, the center reinforcing portion 320 is formed more convexly (thicker) than the other portions.

Here, the center reinforcing portion 320 may be made of a reflective or an opaque material at a surface thereof facing the transmissive lens 120.

This is also to prevent deterioration of a drug solution caused by a laser passing through the separation membrane 300 and reaching the drug when the laser is focused on the space filled with the pressure-generating fluid 101, because the center reinforcing portion 320 is located on the extension of a portion, on which the laser is focused.

The connection reinforcing portion 330 is convexly formed in a shape that connects any one point of the edge reinforcing portion 310 and any one point of the center reinforcing portion 320, and is provided in plural.

The connection reinforcing portion 330 connects the edge reinforcing portion 310 and the center reinforcing portion 320 in a protruding shape, thereby reinforcing non-convex areas.

In other words, the connection reinforcing portion 330 is formed more convexly (thicker) than the other portions.

Here, the edge reinforcing portion 310, the center reinforcing portion 320, and the connection reinforcing portion 330 may have the same thickness or have a thickness different from each other. This is because the life of each portion may be different, so it may be leveled by different thicknesses.

For example, the thickness may be made thinner in the order of the center reinforcing portion 320, the edge reinforcing portion 310, and the connection reinforcing portion 330.

The connection reinforcing portion 330 may be formed radially about the center reinforcing portion 320.

This is to minimize the volume of the connection reinforcing portion 330, so as to disperse the stress (pressure, etc.) applied to the separation membrane 300 and so as to reduce manufacturing cost of the separation membrane 300.

The connection reinforcing portion 330 may be configured such that angles between a connection reinforcing portion and a neighboring connection reinforcing portion are the same.

This is to evenly disperse the stress (pressure, etc.) applied to the separation membrane 300 so as to prolong the life of the separation membrane 300.

As shown in FIGS. 5 to 6, the needleless drug delivery system according to an embodiment of the present invention includes: the upper housing 100 having the transmissive lens 120; the lower housing 200; the separation membrane 300; and a partition membrane 400, wherein the pressure-generating fluid 101 is hermetically filled in a space between the partition membrane 400 and the transmissive lens 120, and a pressure-transmitting fluid 102 is hermetically filled in a space between the partition membrane 400 and the separation membrane 300.

In other words, this is to prevent contamination of the drug due to breakage of the membranes (the separation membrane 300, the partition membrane 400) by using a double membrane structure.

Here, the pressure-generating fluid 101 and the pressure-transmitting fluid 102 may be the same or different liquid.

Further, the pressure-generating fluid 101 may be a liquid or an opaque liquid mixed with a reflector or an opaque material.

This is to prevent deterioration of a drug solution caused by a laser passing through the separation membrane 300 and reaching the drug when the laser is focused on the space filled with the pressure-generating fluid 101.

Further, the pressure-transmitting fluid 102 filled in the space between the partition membrane 400 and the separation membrane 300 may be a liquid or an opaque liquid mixed with a reflector or an opaque material.

This is also to prevent deterioration of a drug solution caused by a laser passing through both the separation membrane 300 and the partition membrane 400 and reaching the drug when the laser is focused on the space filled with the pressure-generating fluid 101.

The upper housing 100 is configured such that a pressure side wall 110 is provided to form a side surface of the upper housing 100 with an end wall closing one end of the pressure side wall 110, and the transmissive lens 120 is provided at the end wall.

The upper housing 100 is provided to form enclosed spaces for respectively allowing the pressure-generating fluid 101 and the pressure-transmitting fluid 102 to be filled therein, and is configured such that the pressure side wall 110 closes the side surface of the upper housing 100, a first end of the upper housing 100, at which the transmissive lens 120 is provided, is closed, the separation membrane 300 closes a second end thereof, and the partition membrane 400 partitions a space between the transmissive lens 120 and the separation membrane 300, thereby forming the enclosed spaces respectively with the pressure-generating fluid 101 and the pressure-transmitting fluid 102 filled therein.

In FIGS. 5 to 6, it is exemplified that the transmissive lens 120 is formed in a convex shape, and the transmissive lens 120 closes a portion of the first end of the pressure side wall 110, but the present invention is not limited thereto, and the transmissive lens 120 may be formed in various shapes such as a planar or a concave shape, capable of projecting light, and the transmissive lens 120 may close the entire first end of the pressure side wall 110.

The lower housing 200 includes: the drug side wall 210 provided to form the side surface of the lower housing; and the discharge nozzle 230 provided by extending from the drug side wall 210 and provided with the discharge hole 231, wherein the lower housing 200 is connected with or extends from the upper housing 100.

The lower housing 200 is provided to form a space for allowing the drug to be filled therein, and is configured such that the drug side wall 210, the discharge nozzle 230, and the separation membrane 300 close the lower housing except the discharge hole 231, thereby forming the space with the drug filled therein.

It is preferred that the discharge hole 231 be formed to have a diameter of 100 μm or less.

When the discharge hole 231 is formed to have a diameter of 100 μm or less, even if the space is filled with the drug, the drug cannot escape through the discharge hole 231 unless a pressure higher than a predetermined pressure is applied.

Here, the upper housing 100 and the lower housing 200 may be integrally formed with each other, or be detachably formed from each other.

The separation membrane 300 is provided between the upper housing 100 and the lower housing 200, and is made of an elastic material to separate the upper housing 100 and the lower housing 200.

In other words, the separation membrane 300 separates the upper housing 100 and the lower housing 200.

Here, the separation membrane 300 may be made of silicone rubber, or the like.

Further, the separation membrane 300 may be made of a reflective or an opaque material.

This is to prevent deterioration of a drug solution caused by a laser passing through the separation membrane 300 and reaching the drug when the laser is focused on the space filled with the pressure-generating fluid.

The partition membrane 400 of elastic material is provided in the upper housing 100 being spaced apart from the separation membrane 300 at a predetermined interval to partition the upper housing 100.

In other words, the separation membrane 300 separates the upper housing 100 and the lower housing 200, and the partition membrane 400 partitions the upper housing 100 into two sections, thereby forming the enclosed space at a first side of the partition membrane 400 (over the partition membrane 400 of FIGS. 5 to 6) with the pressure-generating fluid 101 filled therein, and forming the enclosed space at a second side of the partition membrane 400 (under the partition membrane 400 of FIGS. 5 to 6) with the pressure-transmitting fluid 102 filled therein.

The edge and the center of the separation membrane 300 may be damaged early due to the rapid expansion of the separation membrane. Therefore, it is preferred that the edge and the center of the separation membrane 300 be reinforced, and to achieve this, it is preferable to provide the partition membrane 400 so as to function as a buffer against impact.

In other words, the partition membrane 400 is subjected to a primary impact so that even if the partition membrane 400 is broken, the drug may be prevented from being contaminated by the pressure-generating fluid 101.

Here, the partition membrane 400 may be made of a reflective or an opaque material.

This is to prevent deterioration of a drug solution caused by a laser passing through the partition membrane 400 and reaching the drug when the laser is focused on the space filled with the pressure-generating fluid.

The upper housing 100 may be formed to be capable of being separated into multiple stages (see FIG. 6), and in this case, it is preferred that the partition membrane 400 be interposed at a connection portion of the upper housing 100 (see FIG. 6).

As shown in FIG. 7, the needleless drug delivery system according to an embodiment of the present invention may further include an energy-focusing device 500 configured to focus energy toward a predetermined point of the enclosed space hermetically filled with the pressure-generating fluid 101.

The energy-focusing device 500 refers to a device capable of concentrating energy by using a microwave, a laser, or the like.

In other words, the energy-focusing device 500 concentrates energy, such as a laser, on the pressure-generating fluid 101 to push the drug into the discharge hole 231 by instantaneous volume expansion (pressure increase) due to evaporation of the pressure-generating fluid 101 and transmission of shockwaves, thereby generating a micro jet.

As shown in FIG. 8, the needleless drug delivery system according to an embodiment of the present invention may further include: a drug replenishment hole 220 formed with a channel formed through the drug side wall 210 to supply a drug; and a drug supply unit 600 connected to the drug replenishment hole 220 to supply the drug to a space in the lower housing 200.

In other words, it is possible to replenish the drug to the space to fill the drug by using the drug supply unit 600 connected to the drug replenishment hole 220.

The drug supply unit 600 may replenish the drug with a predetermined level of pressure at which the drug cannot escape through the discharge hole 231.

This is to ensure that the drug is always filled without any additional control.

In other words, if there is no drug in the space, the space may be filled with the drug, but if there is a drug in the space, the space be filled with the drug at a level that does not push the drug into the discharge hole 231.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:
1. A needleless drug delivery system comprising:
an upper housing including: a pressure side wall provided to form a side surface of the upper housing with an end wall closing one end of the pressure side wall; and a transmissive lens provided at the end wall;
a lower housing including: a drug side wall provided to form a side surface of the lower housing; and a discharge nozzle provided by extending from the drug side wall and provided with a discharge hole, wherein the lower housing is connected with or extends from the upper housing; and a separation membrane of elastic material provided between the upper housing and the lower housing to separate the upper housing and the lower housing, wherein a space of the upper housing having the transmissive lens is hermetically filled with a pressure-generating fluid, and the separation membrane includes:

a flat-shape membrane;

an edge reinforcing portion protruding along an edge of the flat-shape membrane;

a center reinforcing portion protruding from a center of the flat-shape membrane; and a plurality of connection reinforcing portions formed on the flat-shape membrane each protruding in a shape that connects any one point of the edge reinforcing portion and the center reinforcing portion, wherein the separation membrane is disposed between a drug solution and the pressure-generation fluid, and wherein the edge reinforcing portion, the center reinforcing portion, and the plurality of connection reinforcing portions are formed on the flat-shape membrane to increase a thickness of the separation membrane partially.

2. The needleless drug delivery system of claim 1, wherein the center reinforcing portion is made of a reflective or an opaque material at a surface thereof facing the transmissive lens.

3. The needleless drug delivery system of claim 1, wherein the connection reinforcing portions are formed radially about the center reinforcing portion.

4. The needleless drug delivery system of claim 1, wherein the connection reinforcing portions are configured such that angles between the connection reinforcing portions are the same.

5. The needleless drug delivery system of claim 1, wherein the separation membrane is made of a reflective or an opaque material.

6. The needleless drug delivery system of claim 1, wherein the pressure-generating fluid is a liquid mixed with a reflector or an opaque material, or an opaque liquid mixed with a reflector or an opaque material.

7. The needleless drug delivery system of claim 1, further comprising:

an energy-focusing device configured to focus energy toward a predetermined point of the space hermetically filled with the pressure-generating fluid.

8. The needleless drug delivery system of claim 1, wherein the lower housing further includes a drug replenishment hole formed with a channel formed through the drug side wall to supply a drug, and the needleless drug delivery system further comprises a drug supply unit connected to the drug replenishment hole to supply the drug.

\* \* \* \* \*